(12) United States Patent
Kurano et al.

(10) Patent No.: US 7,981,648 B2
(45) Date of Patent: Jul. 19, 2011

(54) MICROALGA AND PROCESS FOR PRODUCING HYDROCARBON

(75) Inventors: Norihide Kurano, Iwate (JP); Hiroshi Sekiguchi, Iwate (JP); Akira Sato, Iwate (JP); Satoru Matsuda, Iwate (JP); Kyoko Adachi, Iwate (JP); Mika Atsumi, Iwate (JP)

(73) Assignee: Denso Corporation, Kariya (JP)

( * ) Notice: Subject to any disclaimer, the term of this patent is extended or adjusted under 35 U.S.C. 154(b) by 702 days.

(21) Appl. No.: 11/918,374

(22) PCT Filed: Mar. 24, 2006

(86) PCT No.: PCT/JP2006/306785
§ 371 (c)(1),
(2), (4) Date: Dec. 10, 2007

(87) PCT Pub. No.: WO2006/109588
PCT Pub. Date: Oct. 19, 2006

(65) Prior Publication Data
US 2009/0215140 A1 Aug. 27, 2009

(30) Foreign Application Priority Data

Apr. 12, 2005 (JP) ................... 2005-114404

(51) Int. Cl.
*C12P 5/00* (2006.01)
*C12N 1/12* (2006.01)

(52) U.S. Cl. ............ 435/166; 435/257.1; 435/243

(58) Field of Classification Search ............ None
See application file for complete search history.

(56) References Cited

OTHER PUBLICATIONS (Satoh et al. Plant Cell Physiol. Supplement vol. 47 Mar. 19-21, 2006).*
Fang, J.Y. et al., Fatty acids in *Botryococcus braunii* accelerate topical delivery of flurbiprofen into and across skin., International Journal of Pharmaceutics, 2004, vol. 276, pp. 163 to 173.
Kurano, Norihide et al., Availability of algae and diversity of their products, ("Sorui no Noryoku to Tayona Seisanbutsu"), Annual Meeting of the Molecular Biology Society of Japan Koen Yoshishu, vol. 28, Nov. 25, 2005, p. 54 (W1K-3).
Supplemental European Search Report in corresponding European Application No. 06730733.0.
Metzger, P. et al, "*Botryococcus braunii*: a rich source for hydrocarbons and related ether lipids", Applied Microbiology and Biotechnology, Springer, Berlin, Germany, vol. 66, No. 5, Feb. 1, 2005, pp. 486-496, IP019331745, ISSN: 1432-0614.
Satoh, Akira et al, "Growth and hydrocarbon producing characteristics of a green microalga, Pseudochoricystis ellipsoidea (Trebouxiophyceae)", Plant and Cell Physiology, vol. 47, No. Suppl. S, 2006, p. S92, IP008108761 & 47th Annual Meeting of the Japanese Society of Plant Physiologists, Tsukuba, Japan Mar. 19-21, 2006, ISSN: 0032-0781.
Nakahara, Miho et al; "Choricystis mino as a new symbiont of simultaneous two-species association with Paramexium bursaria and implications for its phylogeny" Symbiosis, vol. 36, No. 2, 2004, pp. 127-151, XP008108760, ISSN: 0334-5114, p. 146.

* cited by examiner

*Primary Examiner* — Robert A Zeman
*Assistant Examiner* — Nina Archie
(74) *Attorney, Agent, or Firm* — Harness, Dickey & Pierce, PLC

(57) ABSTRACT

An object of the present invention is to provide a novel microalga that produces hydrocarbons available as an alternative fuel to a diesel fuel (light oil).
The present invention relates to a novel microalga *Pseudochoricystis ellipsoidea* having the ability to produce hydrocarbons, and to a process for producing hydrocarbons, characterized by culturing a microalga belonging to the genus *Pseudochoricystis* or the genus *Choricystis* having the ability to produce hydrocarbons, and collecting the hydrocarbon from the resulting cultured product.

5 Claims, 15 Drawing Sheets

Nitrogen-sufficient conditions        Nitrogen-deficient conditions

Elapsed time after shift to nitrogen-deficient conditions (hour)

Fig. 13
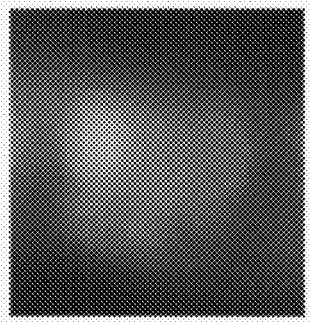
*Choricystis minor* SAG251-1
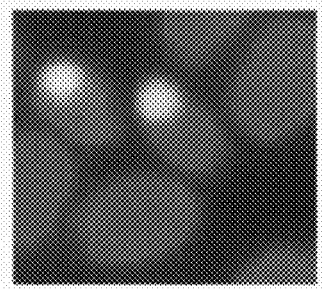
*Choricystis minor* SAG17.98

MICROALGA AND PROCESS FOR PRODUCING HYDROCARBON

TECHNICAL FIELD

The present invention relates to a novel microalga having the ability to produce hydrocarbons and to a process for producing hydrocarbons by use of a microalga.

BACKGROUND ART

Heretofore, some reports have described bacteria having the ability to produce hydrocarbons, including *Vibrio furmissii* M1 (FERM P-18382), which produces $C_{14-22}$ n-alkane by using carbon sources as substrates (M. -O. Park, M. Tanabe, K. Hirata, K. Miyamoto, Isolation and characterization of a bacterium that produces hydrocarbons extracellularly which are equivalent to light oil, Appl. Microbiol. Biotechnol 56 (2001), 448-452; and JP Patent Publication (Kokai) No. 2003-000229A (2003)), and *Pseudomonas anaerooleophila* HD-1 (FERM P-14035), which fixes carbon dioxide and produces n-tetradecane, n-hexadecane, and so on (JP Patent Publication (Kokai) No. 7-194386A (1995)). However, these bacterial strains require organic matter for their hydrocarbon production and have their ability to proliferate or to produce hydrocarbons at unsatisfiable levels. Alternatively, *Klebsiella anaerooleophila* TK-122 (FERM P-16920) is also known, which degrades alkanes or fixes carbon dioxide and produces alkanes, under anaerobic conditions (JP Patent Publication (Kokai) No. 2000-125849A (2000)). This bacterial strain performs degradation and production simultaneously, and its ability to produce hydrocarbons is therefore low in terms of net yields. Moreover, the bacterial strain has been observed to produce hydrocarbons only under oxygen-free conditions. For this reason, its hydrocarbon production under normal aerial conditions requires special culturing and producing apparatuses for keeping oxygen from getting in.

On the other hand, microalgae can perform photosynthesis in the presence of $CO_2$ (inorganic carbon), light energy, and water and produce hydrocarbon-containing organic matter from the $CO_2$. A *Botryococcus braunii* strain is known to intracellularly and extracellularly accumulate linear hydrocarbons as an oil droplet (Metzger and Largeau, *Botryococcus braunii*: a rich source for hydrocarbons and related ether lipids, Appl. Microbiol. Biotechnol 66 (2005)). The feature of *Botryococcus* is that it accumulates hydrocarbons corresponding to heavy oil (30 or more carbon atoms) or longer-chain hydrocarbons. However, no case is known, in which microalgae other than this *Botryococcus* remarkably accumulate linear hydrocarbons.

DISCLOSURE OF THE INVENTION

Thus, an object of the present invention is to provide a novel microalga that produces hydrocarbons, particularly hydrocarbons having carbon atoms ranging from 10 to 25 available as an alternative fuel to a diesel fuel (light oil), by using $CO_2$ as a raw material.

For attaining the object, the present inventors have screened freshwater samples collected from various parts of Japan, and as a result, have successfully isolated a novel microalga having the ability to produce hydrocarbons, thereby completing the present invention.

Namely, the present invention encompasses the inventions described below.

(1) A novel microalga *Pseudochoricystis ellipsoidea* having the ability to produce hydrocarbons.

(2) A novel microalga *Pseudochoricystis ellipsoidea* Sekiguchi et Kurano gen. et sp. nov. MBIC11204 strain having the ability to produce hydrocarbons.

(3) A novel microalga *Pseudochoricystis ellipsoidea* Sekiguchi et Kurano gen. et sp. nov. MBIC11220 strain having the ability to produce hydrocarbons.

(4) The novel microalga according to any of (1) to (3), wherein the hydrocarbon is a saturated or unsaturated aliphatic hydrocarbon having 10 to 25 carbon atoms.

(5) A process for producing hydrocarbons, characterized by culturing a microalga belonging to the genus *Pseudochoricystis* and having the ability to produce hydrocarbons, and collecting the hydrocarbon from the resulting cultured product.

(6) The process according to (5), wherein the microalga is a *Pseudochoricystis ellipsoidea* Sekiguchi et Kurano gen. et sp. nov. MBIC11204 strain.

(7) The process according to (5), wherein the microalga is a *Pseudochoricystis ellipsoidea* Sekiguchi et Kurano gen. et sp. nov. MBIC11220 strain.

(8) A process for producing hydrocarbons, characterized by culturing a microalga belonging to the genus *Choricystis* and having the ability to produce hydrocarbons, and collecting the hydrocarbon from the resulting cultured product.

(9) The process according to (8), wherein the microalga is a *Choricystis minor* SAG251-1 strain or a *Choricystis minor* SAG17.98 strain.

(10) The process according to any of (5) to (9), wherein the hydrocarbon is a saturated or unsaturated aliphatic hydrocarbon having 10 to 25 carbon atoms.

(11) The process according to any of (5) to (10), wherein the culture is performed under nitrogen-deficient conditions.

According to the present invention, a novel microalga having the ability to produce hydrocarbons is provided. The use of the microalga of the present invention makes it possible to produce hydrocarbons available as a biofuel (biodiesel) that becomes an alternative to an existing fossil fuel, as lubricating oil, and as an industrial raw material for plastics, synthetic fibers, and paints. Hydrocarbon production using the microalga of the present invention is performed by photosynthesis and therefore, can reduce carbon dioxide emissions responsible for global warming and produces no environmental loads.

BRIEF DESCRIPTION OF THE DRAWINGS

FIG. 13 shows fluorescence microscope photographs of strains belonging to the genus *Choricystis* (SAG251-1 and SAG17.98 strains) (red color: autofluorescence of chloroplast, yellow granule: oil droplet visualized by Nile Red staining).

Hereinafter the present invention will be described in detail. The present application claims the priority of Japanese Patent Application No. 2005-114404 filed on Apr. 12, 2005 and encompasses contents described in the specification and/or drawings of the patent application.

1. Novel Microalga having Ability to Produce Hydrocarbon

The present invention provides a novel microalga *Pseudochoricystis ellipsoidea* having the ability to produce hydrocarbons.

Examples of. such a microorganism can include a *Pseudochoricystis ellipsoidea* Sekiguchi et Kurano gen. et sp. nov. MBIC11204 strain and a *Pseudochoricystis ellipsoidea* Sekiguchi et Kurano gen. et sp. nov. MBIC11220 strain, isolated from freshwater samples by the present inventors.

These microalgal strains were selected by adding an IMK medium (manufactured by Nihon Pharmaceutical) having the composition shown in Table 1 below to 30 milliliters each of hot spring water samples collected from various parts of Japan, then statically culturing the samples at approximately 20° C. under irradiation with the light of a fluorescent lamp, and observing the resulting samples under a microscope.

TABLE 1

| IMK medium composition | |
|---|---|
| NaNO$_3$ | 200 mg |
| Na$_2$HPO$_4$ | 1.4 mg |
| K$_2$HPO$_4$ | 5 mg |
| NH$_4$Cl | 2.68 mg |
| Thiamin-HCl | 0.2 mg |
| Biotin | 0.0015 mg |
| Vitamin B$_{12}$ | 0.0015 mg |

TABLE 1-continued

| IMK medium composition | |
|---|---|
| Mn-EDTA | 0.332 mg |
| Fe-EDTA | 5.2 mg |
| Na$_2$-EDTA | 37 mg |
| MnCl$_2$•4H$_2$O | 0.18 mg |
| ZnSO$_4$•7H$_2$O | 0.024 mg |
| CoSO$_4$•7H$_2$O | 0.012 mg |
| Na$_2$MoO$_4$•2H$_2$O | 0.0072 mg |
| CuSO$_4$•5H$_2$O | 0.0025 mg |
| Na$_2$SeO$_3$ | 0.002 mg |
| Desalted water | 1000 ml |
| pH 8.0 | |

Figure 1:
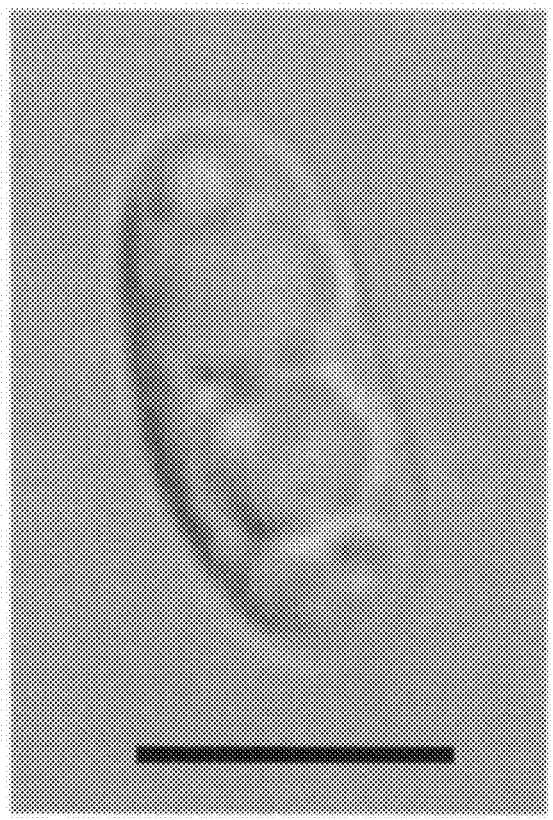
FIG. 1 shows an optical microscope photograph of an MBIC11204 strain (the black line denotes 1 μm).

The phycological properties of the MBIC11204 strain are as follows:

A. Morphological Properties (1) A vegetative cell is an ellipsoidal shape or a slightly curved kidney shape with rounded ends. The minor axis and major axis thereof are 1 to 2 μm and 3 to 4 μm, respectively (FIG. 1). The cell has no flagella and exhibits no motility. The cells are agglutinated under alkaline conditions.

Figure 2:
FIG. 2 shows an electron micrograph of an ultra-thin section of the MBIC11204 strain (the black line denotes 1 μm. C: chloroplast, V: vacuole).

(2) The vegetative cell is enclosed with a cell wall and contains one nucleus and one chloroplast. In addition, a mitochondrion, Golgi body, vacuole, oil droplet, and so on, are observed therein. No pyrenoid are observed in the chloroplast (FIG. 2).

Figure 3:
FIG. 3 shows an electron micrograph of an ultra-thin section of the MBIC11204 strain that reproduces by means of a tetraspore (the black line denotes 1 μm).

B. Reproduction Manner (1) Four endospores are formed in the vegetative cell (FIG. 3) and uniformly distributed within the cell. The endospore intracellularly has one nucleus and one chloroplast.

Figure 4:
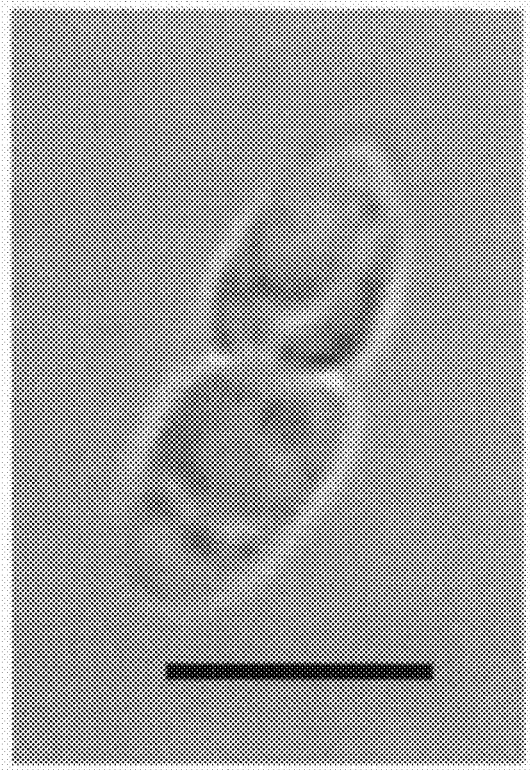
FIG. 4 shows an optical microscope photograph of the MBIC11204 strain that proliferates by means of binary fission (the black line denotes 1 μm).

(2) The cell also proliferates by means of binary fission (FIG. 4).

C. Physiological and Biochemical Properties (1) Culture medium : the strain can be grown in a culture medium basically containing fresh water.

(2) Photosynthetic capacity: the strain can be grown photoautotrophically through photosynthesis.

(3) Pigment contained therein: chlorophyll a, chlorophyll b, and other carotenoids.

(4) Assimilation and reserve substance: starch.

(5) Growth temperature range: 15° C. to 30° C. (optimal temperature: 25° C.).

(6) Growth pH range: pH 6.0 to 10.0 (optimal pH: 7.0).

Figure 5:
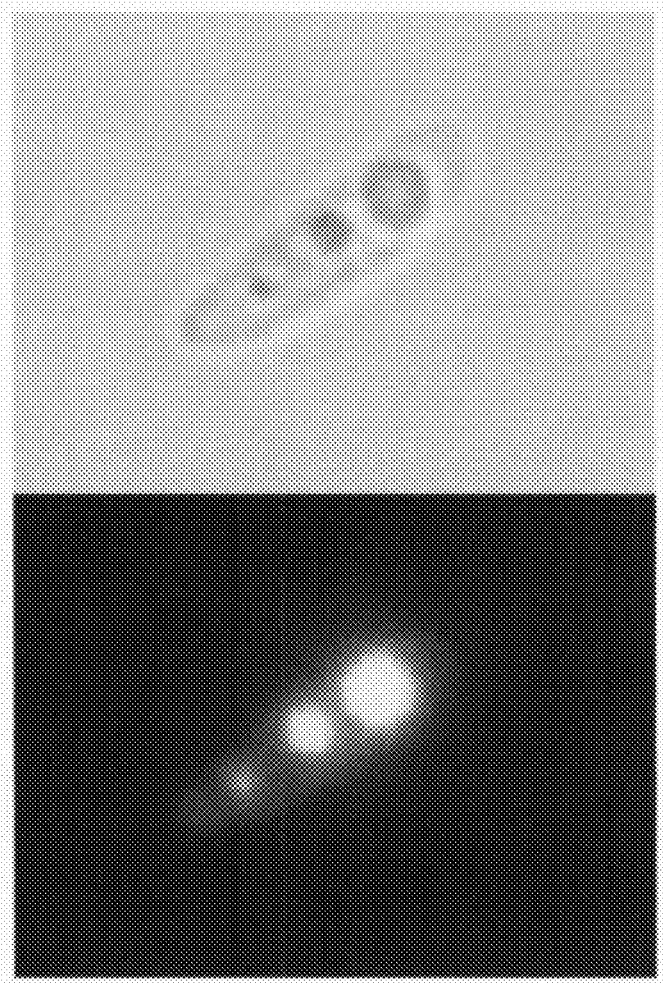
FIG. 5 shows a fluorescence microscope photograph of the MBIC11204 strain (upper view: bright field, lower view: fluorescence field, bright fluorescence: intracellular oil droplet visualized by Nile Red staining, dim region: autofluorescence of chloroplast).
Figure 6:
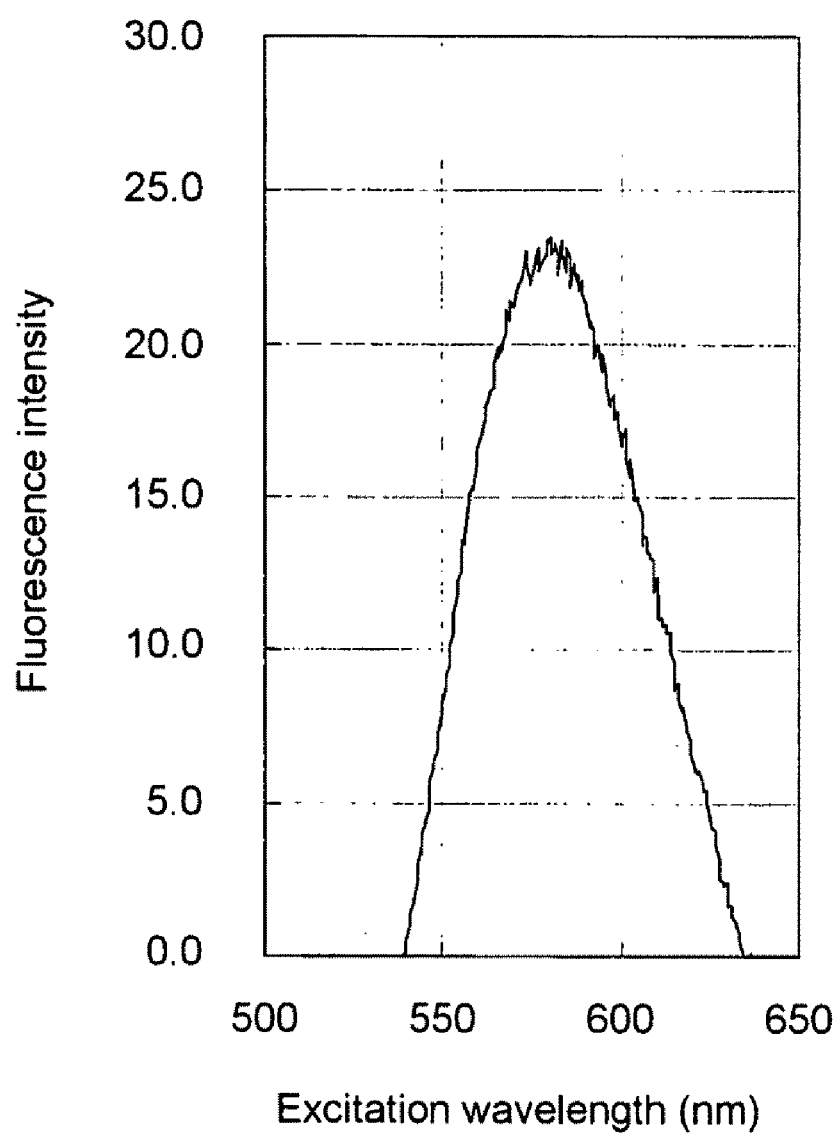
FIG. 6 shows a fluorescence pattern (excitation wavelength: 488 nm) of the MBIC 11204 strain stained with Nile Red.

(7) Oil droplets present in the cell exhibit orange fluorescence by fluorescent staining with Nile Red (FIG. 5). FIG. 6 shows a fluorescence pattern of typical neutral lipid of the MBIC 11204 strain stained with Nile Red.

As described above, the MBIC11204 strain is an ellipsoidal shape or a slightly curved kidney shape and contains chlorophyll a and chlorophyll b as primary photosynthetic pigments. Moreover, the strain has no swarmer stage and reproduces by means of binary fission or tetraspore formation. Furthermore, the strain has a pyrenoid-free chloroplast.

Figure 7:
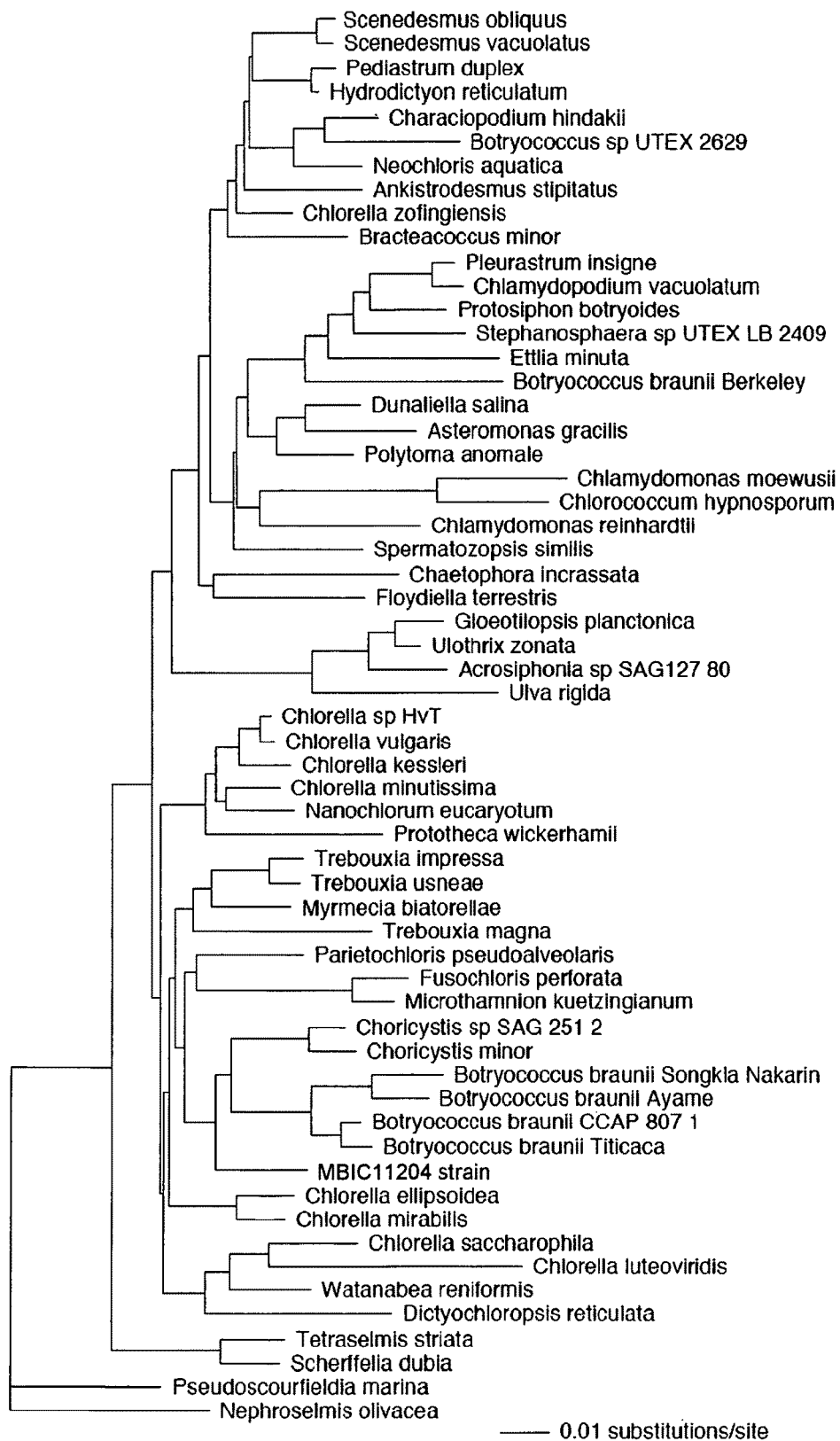
FIG. 7 shows a molecular phylogenic tree of green plants (partial 18S rDNA sequence, NJ method).
Figure 8:
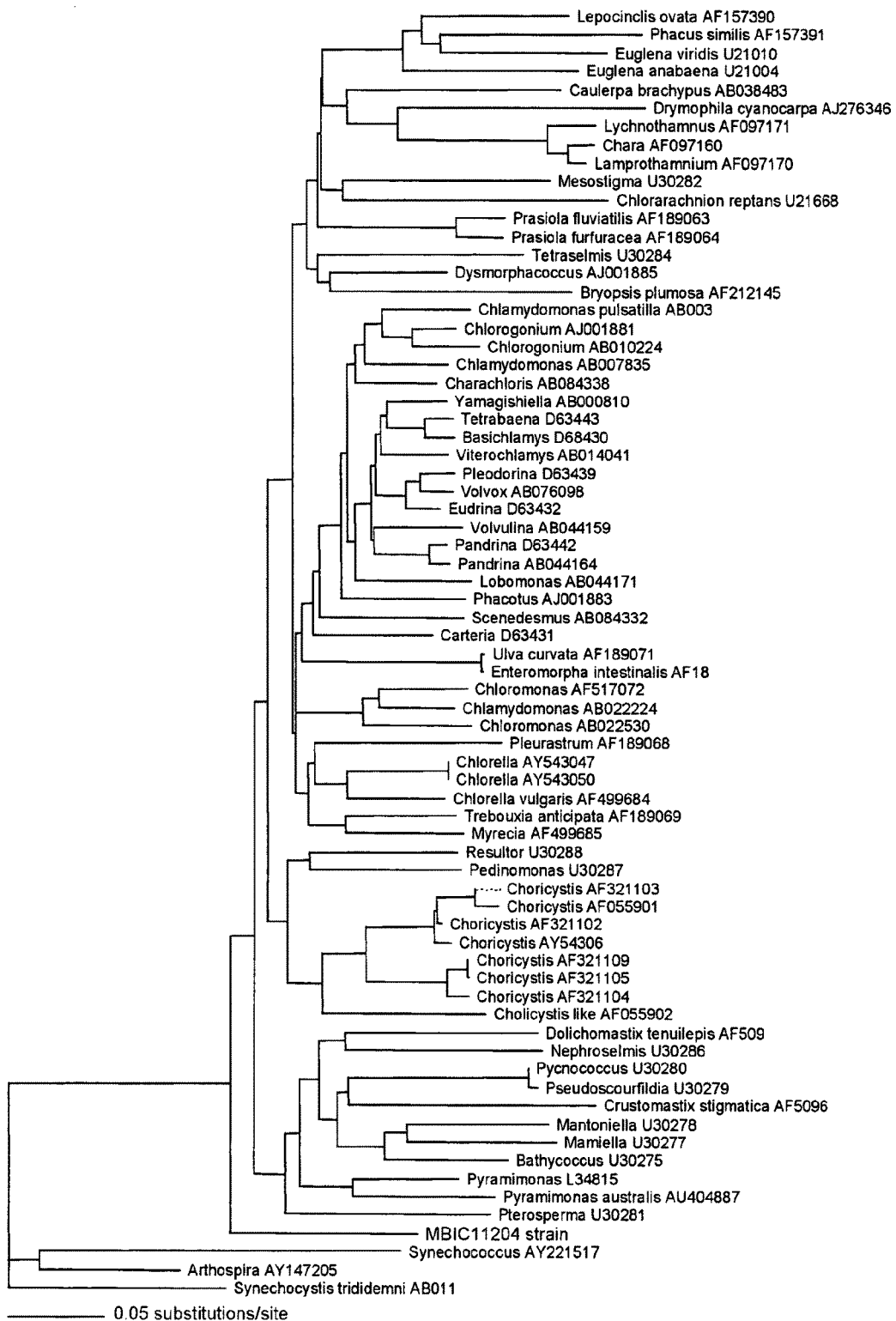
FIG. 8 shows a molecular phylogenic tree of green plants in general (partial rbcL sequence, NJ method). Three *Cyanobacteria* strains were used as an out-group.

From these points of view, the MBIC11204 strain was in good morphological agreement with the known genus *Choricystis* of the class *Trebouxiophyceae* and was presumed to belong to the genus *Choricystis*. However, molecular phylogenic analysis using the 18S rDNA gene as an index showed no relationship between the MBIC11204 strain and the known genus *Choricystis* (FIG. 7). On the other hand, molecular phylogenic analysis using the partial sequence of the Rubisco large subunit gene (rbcL) as an index revealed that the MBIC11204 strain is located at a root of green plants in general (FIG. 8). The 18S rDNA nucleotide sequence of the MBIC11204 strain is shown in SEQ ID NO: 1 of the sequence listing, while the Rubisco large subunit (rbcL) nucleotide sequence of the MBIC11204 strain is shown in SEQ ID NO: 2 of the sequence listing. In the same analyses, the genus *Choricystis* constitutes a single clade, and the MBIC11204 strain is located at a position far away from the clade. Moreover, the MBIC11204 strain also differs largely from the type strains of the class *Trebouxiophyceae* and from the genus *Chlorella*.

Thus, the MBIC11204 strain was judged as a new genus and new species of microalgal strain, which is characterized by (i) being morphologically similar to the genus *Choricystis* and however, not belonging to the genus *Choricystis* in the phylogenetic analysis based on the 18S rDNA gene, (ii) being located at a root of green plants in the phylogenetic analysis based on the rbcL gene, and (iii) containing linear hydrocarbons. Accordingly, the strain was designated as *Pseudochoricystis ellipsoidea* Sekiguchi et Kurano gen. et sp. nov. MBIC11204. The genus name means that the strain is morphologically similar to the genus *Choricystis*. The species name is derived from the ellipsoidal shape of its cell.

Figure 15:
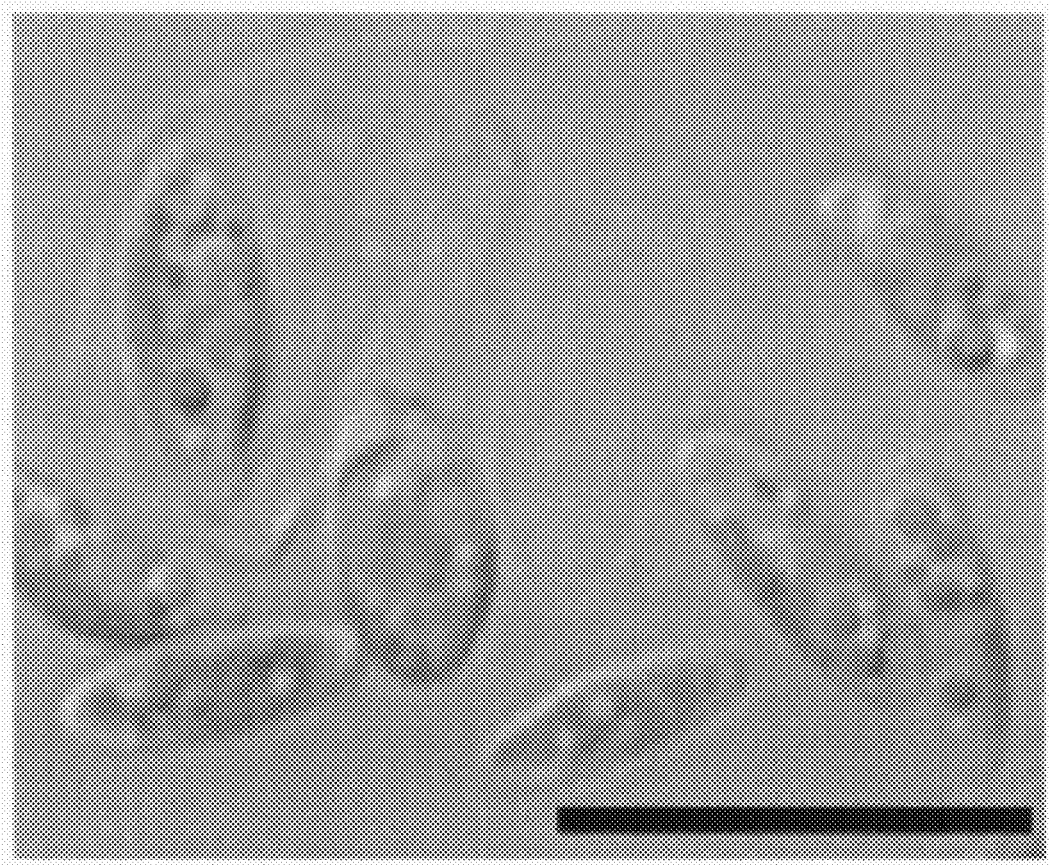
FIG. 15 shows an optical microscope photograph of the MBIC11220 strain (the black line denotes 10 μm).

On the other hand, the MBIC11220 strain is an ellipsoidal shape or a slightly curved kidney shape, as with the MBIC11204 strain (FIG. 15), and its other phycological properties were in agreement with the MBIC11204 strain. Moreover, the 18S rDNA nucleotide sequence (SEQ ID NO: 3 of the sequence listing) and Rubisco large subunit (rbcL) nucleotide sequence (SEQ ID NO: 4 of the sequence listing) of the MBIC11220 strain were determined. Molecular phylogenic analysis using the 18S rDNA gene as an index as well as molecular phylogenic analysis using the partial sequence of the Rubisco large subunit gene (rbcL) as an index was performed in the same way. The characteristics of the MBIC11220 strain were also in agreement with the characteristics (i) to (iii) of the MBIC11204 strain, in light of the results of the molecular phylogenic analyses and linear hydrocarbon production. Thus, the MBIC11220 strain was also judged as a new genus and new species of microalgal strain and designated as *Pseudochoricystis ellipsoidea* Sekiguchi et Kurano gen. et sp. nov. MBIC11220.

The MBIC11204 strain was deposited on Feb. 15, 2005 as deposition No. FERM P-20401 in International Patent Organism Depositary (IPOD), National Institute of Advanced Industrial Science and Technology (Tsukuba Central 6, 1-1-1 Higashi, Tsukuba, Ibaraki, Japan), and was transferred to the international deposit on Jan. 18, 2006 as deposition No. FERM BP-10484 under the terms of the Budapest Treaty.

Alternatively, the MBIC11220 strain was deposited on Jan. 18, 2006 as deposition No. FERM BP-10485 in International Patent Organism Depositary (IPOD), National Institute of Advanced Industrial Science and Technology (Tsukuba Central 6, 1-1-1 Higashi, Tsukuba, Ibaraki, Japan) under the Budapest Treaty.

2. Process for producing hydrocarbon by use of microalga

The MBIC11204 strain was confirmed to produce 9 kinds of hydrocarbons, as a result of gas chromatography mass spectrometry (GC-MS). All of these hydrocarbons are aliphatic hydrocarbons, of which 6 kinds are n-heptadecene ($C_{17}H_{34}$), n-heptadecane ($C_{17}H_{36}$), n-octadecene ($C_{18}H_{36}$), n-octadecane ($C_{18}H_{38}$), n-nonadecene ($C_{19}H_{38}$), and n-nonadecane ($C_{19}H_{40}$), and the remaining 3 kinds are n-eicosadienes ($C_{20}H_{38}$) whose double bonds are present at 2 sites, and however, their position cannot be identified (Table 6). Alternatively, the MBIC11220 strain was confirmed to produce 4 kinds of hydrocarbons, n-heptadecene ($C_{17}H_{34}$), n-heptadecane ($C_{17}H_{36}$), n-nonadecene ($C_{19}H_{38}$), and n-nonadecane ($C_{19}H_{40}$) (Table 6).

Figure 9:
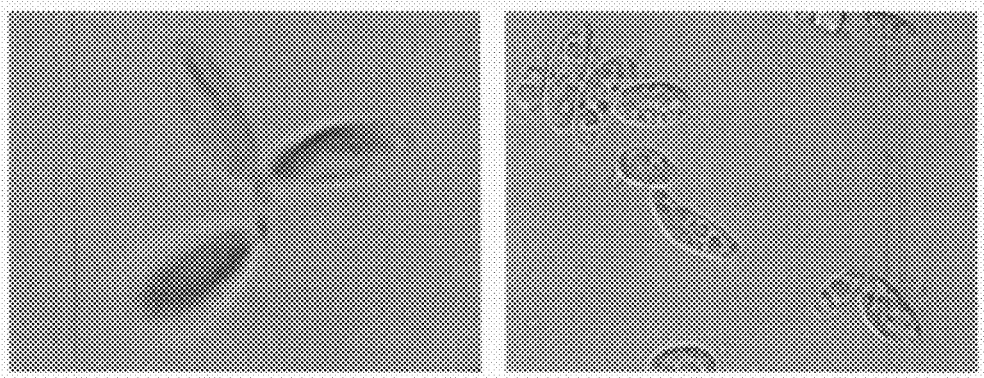
FIG. 9 shows an optical microscope photograph of MBIC11204 strain cells under nitrogen-sufficient conditions (left) and nitrogen-deficient conditions (right). The remarkable accumulation of oil contents is observed under the nitrogen-deficient conditions.
Figure 10:
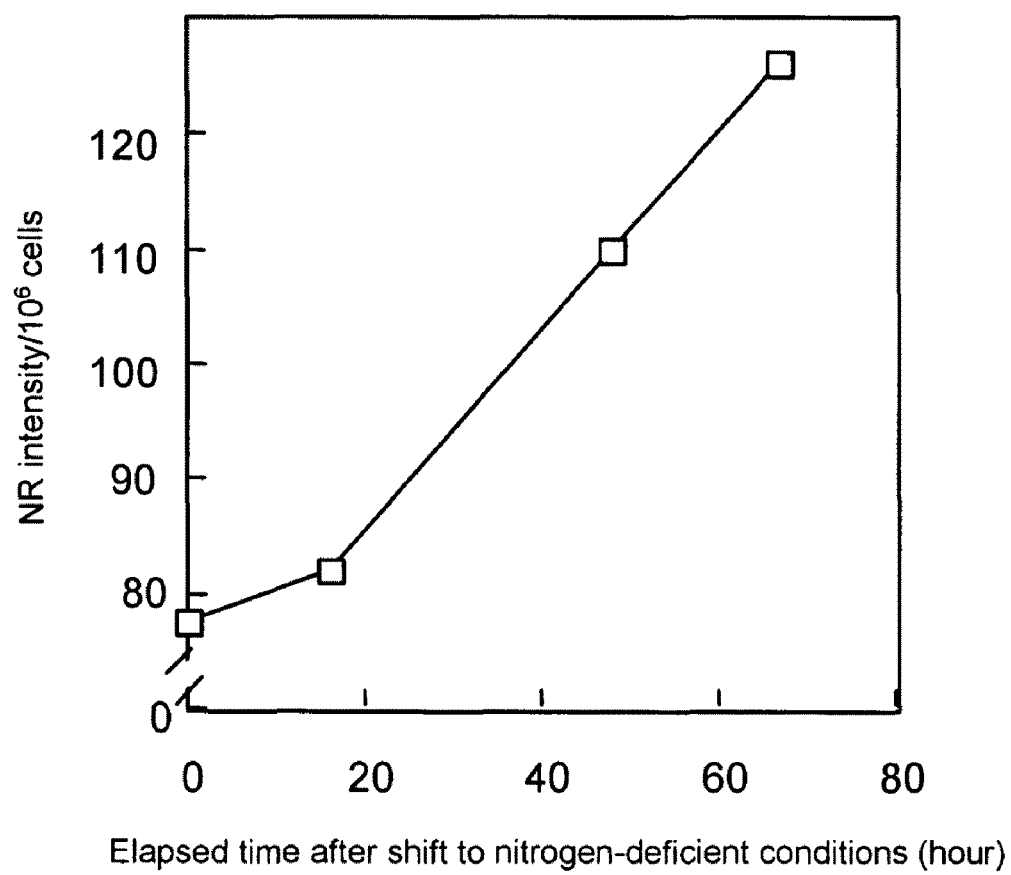
FIG. 10 shows a rising curve of the oil contents after a shift to nitrogen-deficient conditions. The horizontal axis denotes elapsed time after a shift to nitrogen-deficient conditions, while the longitudinal axis denotes Nile Red fluorescence intensity per unit cell. Nile Red fluorescence serves as an index of oil contents.

As shown in FIG. 9, the hydrocarbon oil droplet content of the MBIC11204 strain considerably increases under nitrogen-deficient conditions. In addition, when the fluorescence intensity of the cell stained with Nile Red was measured, the fluorescence intensity per unit cell increased after a shift to the nitrogen-deficient conditions (FIG. 10). Because this Nile Red fluorescence reflects the hydrocarbon content of the cell, the nitrogen-deficient conditions are said to be effective as means for increasing yields in hydrocarbon production using the MBIC11204 strain.

From these points of view, the present invention provides a process for producing hydrocarbons, characterized by culturing a microalga belonging to the genus *Pseudochoricystis* and having the ability to produce hydrocarbons, and collecting the hydrocarbon from the resulting cultured product.

Moreover, similar hydrocarbon oil droplets were also observed in cultured cells of microalgal strains belonging to the genus *Choricystis* (FIG. 13). As a result of analysis, these hydrocarbon oil droplets consisted of 3 kinds of hydrocarbons, n-heptadecane ($C_{17}H_{36}$), n-nonadecene ($C_{19}H_{38}$), and n-heneicosene ($C_{21}H_{42}$), in the *Choricystis minor* SAG251-1 strain, and 4 kinds of hydrocarbons, n-heptadecane ($C_{17}H_{36}$), n-nonadecene ($C_{19}H_{38}$), n-heneicosene ($C_{21}H_{42}$), and n-tricosene ($C_{23}H_{46}$), in the *Choricystis minor* SAG17.98 strain (Table 6).

Thus, the present invention also provides a process for producing hydrocarbons, characterized by culturing a microalga belonging to the genus *Choricystis* and having the ability to produce hydrocarbons, and collecting the hydrocarbon from the resulting cultured product.

All the hydrocarbons produced by the processes include one kind of saturated or unsaturated aliphatic hydrocarbon having 10 to 25 carbon atoms, or a mixture of two kinds thereof. Namely, although conventional methods using a microalga merely produce hydrocarbons having carbon atoms corresponding to heavy oil, the process of the present invention using the microalga makes it possible to produce hydrocarbons having carbon atoms corresponding to light oil.

A medium for culturing the microalga may be any of those typically used in microalga culture. For example, any of media for freshwater or marine microalgae known in the art containing a variety of nutrient salts, salts of trace metals, vitamins, and so on can be employed. Examples of the nutritive salts include: nitrogen sources such as $NaNO_3$, $KNO_3$, $NH_4Cl$, and urea; and phosphorus sources such as $K_2HPO_4$, $KH_2PO_4$, and sodium glycerophosphate. Examples of the trace metals include iron, magnesium, manganese, calcium, and zinc. Examples of the vitamins include vitamin $B_1$ and vitamin $B_{12}$. The culture may be performed by procedures of stirring with carbon dioxide supply under aeration conditions. In these procedures, the microalga is cultured under light irradiation that adopts a light-dark cycle such as 12-hour light (a fluorescent lamp) and 12-hour dark conditions, or under continuous light irradiation. Culture conditions are not particularly limited within a range that does not adversely affect the growth of the microalga. For example, the pH of the culture medium adjusted to 7 to 9 and a culture temperature adjusted to 20 to 30° C. are preferred. When the culture is performed under conditions as described above, the hydrocarbons can be collected after approximately 6 to 8 days into the culture.

More specifically, the MBIC11204 strain can be cultured in a culture medium prepared by steam-sterilizing the above-described commercially available IMK medium (manufactured by Nihon Pharmaceutical) dissolved at the respective specified concentrations in desalted water, and then adding a variety of buffer solutions thereto. The MBIC11204 strain is inoculated to this culture medium and can be cultured statically or with shaking or aeration, at 25° C. under irradiation with the light of a fluorescent lamp (under continuous light irradiation or under light-dark cycle). The addition of approximately 1 to 5% carbon dioxide to the air environment of the culture is preferred because the growth of the strain is promoted. Alternatively, a medium for known freshwater microalgae may also be used. Furthermore, an agar plate medium prepared based on the medium for known freshwater microalgae is also available.

The produced hydrocarbon can be collected from the cells of the cultured microalga. This collection may be performed by a method in which the cells are disrupted by a general technique such as French press or homogenizers to extract the hydrocarbon with an organic solvent such as n-hexane, or a method in which the cells are collected onto a filter such as glass fiber and dried to extract the hydrocarbon with an organic solvent or the like. In an alternative method that can collect the hydrocarbon, the cells are collected by centrifugation, then freeze-dried, and powdered, followed by extraction from the powder with an organic solvent. After extraction, the solvent is evaporated under reduced pressure or normal pressure, or by heating, or at room temperature, thereby giving the hydrocarbon of interest.

BEST MODE FOR CARRYING OUT THE INVENTION

Hereinafter, the present invention will be described more fully with reference to Examples. However, the present invention is not intended to be limited to these Examples.

EXAMPLE 1

An A5 medium having the composition shown in Table 2 below was prepared using deionized water. This A5 medium was placed in a flat glass flask (working volume: 500 ml) and autoclaved.

TABLE 2

A5 medium composition

| | |
|---|---|
| NaNO$_3$ | 150 mg |
| MgSO$_4$•7H$_2$O | 10 mg |
| KH$_2$PO$_4$ | 3.5 mg |
| K$_2$HPO$_4$ | 4.5 mg |
| CaCl$_2$•2H$_2$O | 0.9 mg |
| Fe-EDTA | 1.2 ml |
| Metal solution | 0.1 ml |
| Desalted water | 99.8 ml |
| pH | 7.5 |

Metal solution

| | |
|---|---|
| H$_3$BO$_3$ | 7 mg |
| MnSO$_4$•7H$_2$O | 15 mg |
| ZnSO$_4$•7H$_2$O | 30 mg |
| CuSO$_4$•5H$_2$O | 30 mg |
| Na$_2$MoO$_4$ | 0.3 mg |
| CoCl$_2$ | 7 mg |
| Desalted water | 100 ml |

Figure 11:
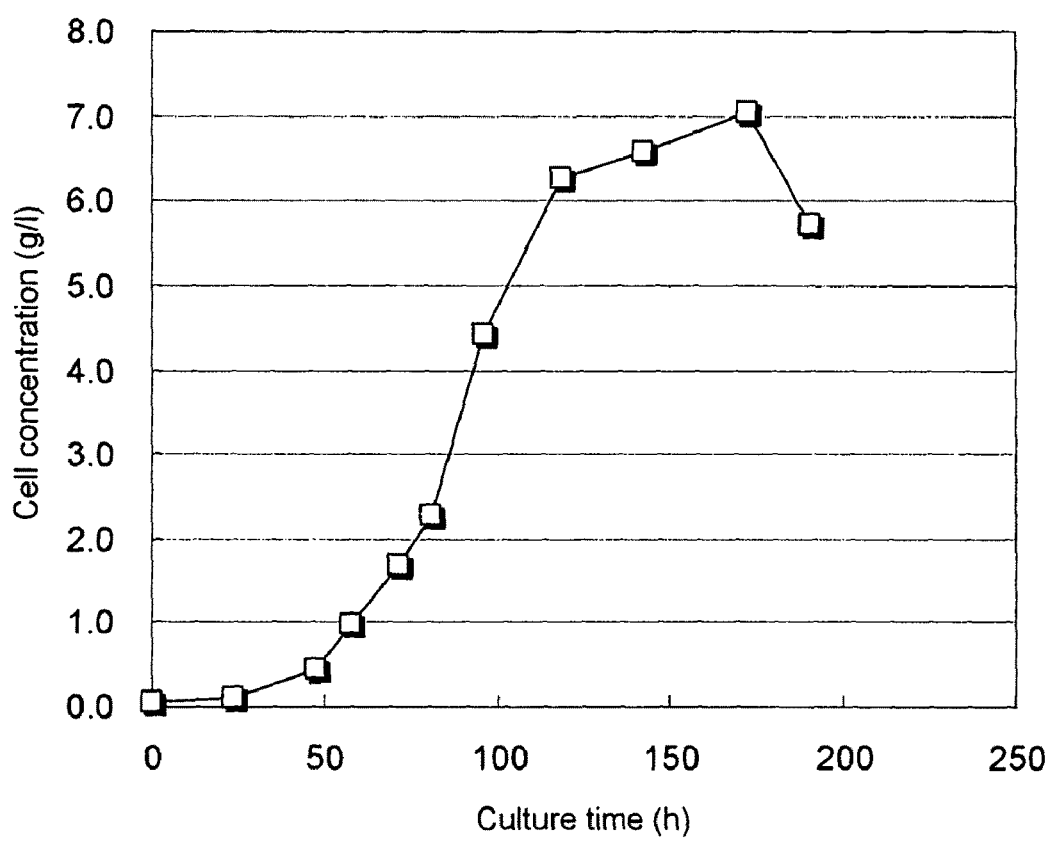
FIG. 11 shows a growth curve of the MBIC11204 strain, with its dry weight as an index.

A *Pseudochoricystis ellipsoidea* Sekiguchi et Kurano gen. et sp. nov. MBIC11204 strain (hereinafter, referred to as the MBIC11204 strain) was inoculated to the A5 medium. A breathable stopper Was put on the flask, and the culture medium in the flask was stirred and simultaneously aerated with air supplemented with 3% CO$_2$. In this procedure, the flask was irradiated with the light of a white fluorescent lamp from around the flask, and its temperature was adjusted to approximately 28° C. by dipping the flask in a temperature-controlled water bath. The dry weight of the cultured cells was measured over time as an index of the growth of the MBIC11204 strain. These results are shown in FIG. 11. A specific growth rate in the logarithmic growth phase was 0.079 h$^{-1}$, with 1 cell division every 8.8 hours.

The cells in 400 ml of the obtained culture medium were centrifuged at 15,000 rpm for 10 minutes and washed twice with a nitrogen-deficient medium of the same composition as the A5 medium except for NaNO$_3$. The resulting cells were cultured for 3 days in the nitrogen-deficient medium under the same conditions. As a result, the accumulation of considerable amounts of hydrocarbons was confirmed under an optical microscope (FIG. 9).

EXAMPLE 2

The cultured microalgal cells (300 ml) obtained in Example 1 were collected by centrifugation and then freeze-dried. The dry weight of the microalgal cells was 721.7 mg under the nitrogen-deficient conditions and 884.7 mg under the nitrogen-containing conditions. Fat-soluble compounds were semi-purified with 10 ml of n-hexane per 200 mg of the dried microalgal cells. The 10-ml aliquot of the extract was then condensed to 1 ml or less using nitrogen gas. Before measurement, the resulting condensate was brought to 1 ml and used as a sample for GC-MS analysis.

A capillary column used for GC-MS analysis was DB-5 (J&W; 30 m×0.25 mm). A measurement instrument used was GCMS-QP5000 (Shimadzu Corp). Ionization methods used were electron ionization (EI) and chemical ionization (CI) methods. A linear saturated hydrocarbon mixture (C11, C13, C15, C17, C19, C20, C22, C24, C26, C28, C30) standard sample (GL Sciences) was used for identifying components.

GC-MS conditions are as follows:
Injector temperature: 280° C.
Amount of sample injected: 1 μl
Injection mode: splitless mode
Interface temperature: 300° C.
Sampling time: 0.5 min
Column inlet pressure: 100 kPa
Gas flow rate: 50.0 ml/min
Carrier gas: helium gas
Temperature rising conditions: temperature is maintained at 50° C. for 2 minutes from the start of analysis, then increased to 300° C. at a rate of 6° C./min, and maintained at 300° C. for 18 minutes.
Ionization voltage (EI): 70 eV
Reaction gas (CI): methane
Scanned range: m/z 50 to 500

As a result of the GC-MS (EI) analysis, components contained in the sample were presumed from the fragment pattern to be 9 kinds of hydrocarbons, of which 6 kinds were n-heptadecene (C$_{17}$H$_{34}$), n-heptadecane (C$_{17}$H$_{36}$), n-octadecene (C$_{18}$H$_{36}$), n-octadecane (C$_{18}$H$_{38}$), n-nonadecene (C$_{19}$H$_{38}$), and n-nonadecane (C$_{19}$H$_{40}$), and the remaining 3 kinds were n-eicosadienes (C$_{20}$H$_{38}$). However, the position of double bonds in the n-eicosadienes could not be identified (Table 6).

Alternatively, the MBIC11204 strain was cultured for 7 days in an MC medium (Table 4 below) and transferred to a medium of the same composition as the MC medium except for KNO$_3$. The culture medium was collected after an appropriate time interval and supplemented with dimethyl sulfoxide (DMSO) at the final concentration of 20%, followed by stirring. After 5 minutes, a Nile Red solution (final concentration: 5 μg/ml) was added thereto and stirred. The resulting solution was further left for 5 minutes, followed by the measurement of fluorescence intensity (excitation: 488 nm, emission: 580 nm). The rising pattern of the fluorescence intensity per unit cell is shown in FIG. 10. Because this fluorescence intensity reflects the amount of substances stained with Nile Red, that is, the amount of hydrocarbons in the cells, a rise in the fluorescence intensity means increase in the amount of hydrocarbons. Rapid increase in the amount of hydrocarbons was shown after a shift to the nitrogen-deficient conditions.

EXAMPLE 3

The MBIC11204 strain was inoculated to each of culture media (already autoclaved) prepared by respectively adding 3 kinds of buffer solutions (50 mM MES (pH 5.5), 50 mM MOPS (pH 7.0), and 50 mM CHES (pH 9.0)) to a C medium having the composition shown in Table 3 below, and cultured in the same way as in Example 1. In this way, the influence of pH of the culture medium on cell growth was evaluated.

Figure 12:
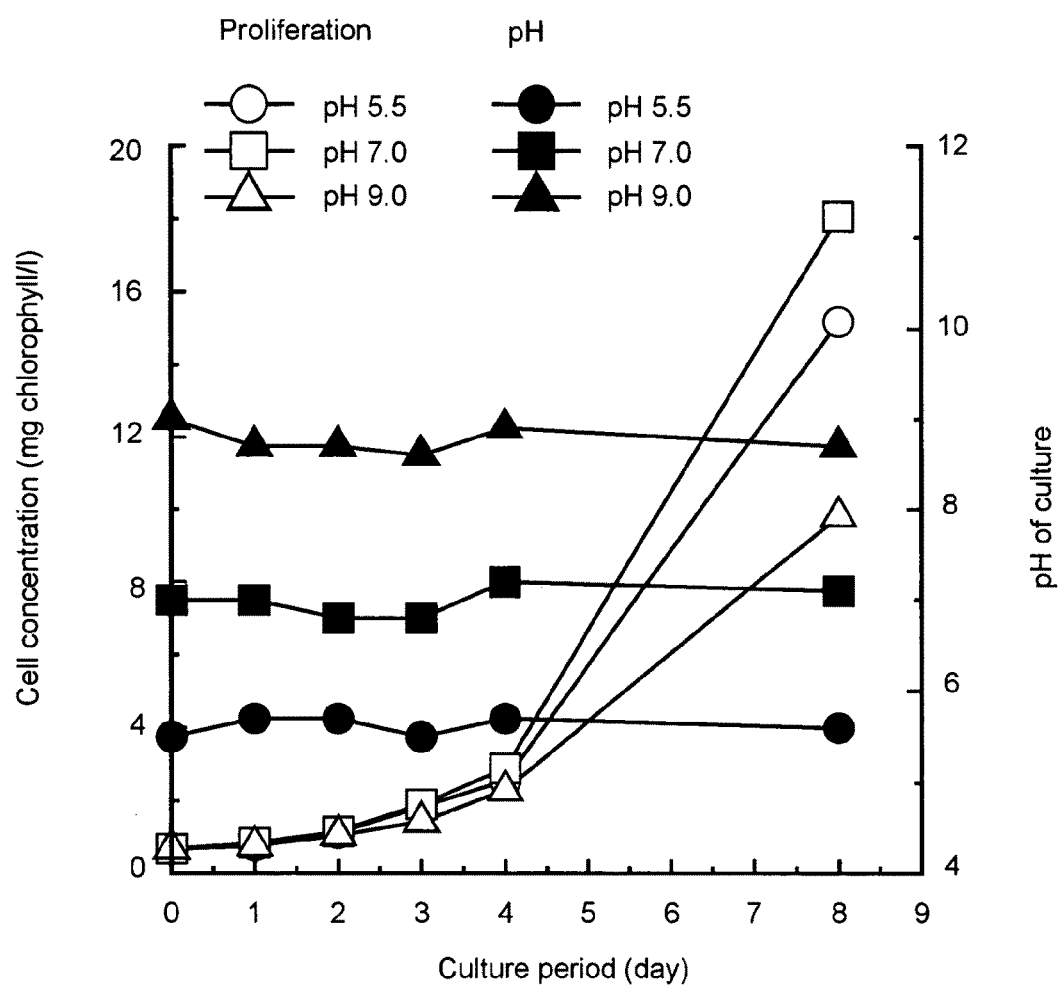
FIG. 12 shows a growth characteristics of the MBIC11204 strain relative to pH (open symbols:growth, solid symbols: pH).

As shown in FIG. 12, the most favorable growth was obtained at pH 7.0. Because the concentrations of the buffer solutions were set to 50 mM, pH was stable during the culture.

TABLE 3

| C medium composition | |
|---|---|
| $Ca(NO_3)_2 \cdot 4H_2O$ | 15 mg |
| $KNO_3$ | 10 mg |
| $MgSO_4 \cdot 7H_2O$ | 4 mg |
| Sodium β-glycerophosphate | 5 mg |
| Vitamin $B_1$ | 1 μg |
| Vitamin $B_{12}$ | 0.01 μg |
| Biotin | 0.01 μg |
| Tris buffer | 50 mg |
| PIV metal solution | 0.3 ml |
| Desalted water | 99.7 ml |
| PIV metal solution | |
| $FeCl_3 \cdot 6H_2O$ | 19.6 mg |
| $MnCl_2 \cdot 4H_2O$ | 3.6 mg |
| $ZnCl_2$ | 1.05 mg |
| $CoCl_2 \cdot 6H_2O$ | 0.4 mg |
| $Na_2MoO_4 \cdot 2H_2O$ | 0.25 mg |
| $Na_2EDTA \cdot 2H_2O$ | 100 mg |
| Desalted water | 100 ml |

EXAMPLE 4

An experiment was conducted for determining which of an MC medium having the composition shown in Table 4 below and the C medium used in Example 3 is suitable for the culture of the MBIC11204 strain. At the same time, the effect of adding $CO_2$ to the air environment of the culture was confirmed.

Two culture bottles containing the autoclaved MC medium and two culture bottles containing the autoclaved C medium were prepared. One of the two culture bottles was aerated with only air, and the other was aerated with mixture gas of air supplemented with 3% $CO_2$. The MBIC11204 strain was cultured therein for 6 days under the same conditions as in Example 1.

TABLE 4

| MC medium composition | |
|---|---|
| $KNO_3$ | 125 mg |
| $MgSO_4 \cdot 7H_2O$ | 125 mg |
| $KH_2PO_4$ | 125 mg |
| Fe solution | 0.1 ml |
| $A_5$ metal solution | 0.1 ml |
| Desalted water | 99.8 ml |
| pH | 6.0 |

TABLE 4-continued

| Fe solution | |
|---|---|
| $FeSO_4 \cdot 7H_2O$ | 1.0 g |
| Desalted water | 500 ml |
| $H_2SO_4$ | 2 drops |
| $A_5$ metal solution | |
| $H_3BO_3$ | 286 mg |
| $MnSO_4 \cdot 7H_2O$ | 250 mg |
| $ZnSO_4 \cdot 7H_2O$ | 22.2 mg |
| $CuSO_4 \cdot 5H_2O$ | 7.9 mg |
| $Na_2MoO_4$ | 2.1 mg |
| Desalted water | 100 ml |

The result is shown in Table 5. The best growth was obtained under the condition using the MC medium and the addition of 3% $CO_2$ (34.8-fold chlorophyll concentration). The addition of $CO_2$ was confirmed to serve as a positive factor for the MC medium, whereas the culture using only air produced a similar growth result to that of the culture using the addition of $CO_2$, for the C medium.

TABLE 5

Variations of growth of MBIC11204 strain depending on kinds of media and $CO_2$ concentrations

| | | Chlorophyll concentration (mg chlorophyll/l) | | |
|---|---|---|---|---|
| Medium | Aeration | Day 0 | Day 6 | Growth degree |
| MC | $CO_2$ | 0.8 | 27.8 | 34.8 |
| MC | Air | 0.8 | 14.5 | 18.1 |
| C | $CO_2$ | 0.8 | 20.4 | 25.5 |
| C | Air | 0.8 | 20.1 | 25.1 |

EXAMPLE 5

Cells of microalgae deposited in Culture Collection of Algae (SAG) at the University of Gottingen were directly stained with Nile Red and observed. As a result, *Choricystis minor* SAG251-1 and *Choricystis minor* SAG17.98 strains were confirmed to develop orange fluorescence and remarkably contain oil droplets (FIG. 13).

When these oil droplets were analyzed by MS-GS under the same conditions as in Example 2, the oil droplets in the *Choricystis minor* SAG251-1 strain were presumed from the fragment pattern to be 3 kinds of hydrocarbons, n-heptadecane ($C_{17}H_{36}$), n-nonadecene ($C_{19}H_{38}$), and n-heneicosene ($C_{21}H_{42}$). Similarly, the oil droplets in the *Choricystis minor* SAG17.98 strain were presumed to be 4 kinds of hydrocarbons, n-heptadecane ($C_{17}H_{36}$), n-nonadecene ($C_{19}H_{38}$), n-heneicosene ($C_{21}H_{42}$), and n-tricosene ($C_{23}H_{46}$) (Table 6).

EXAMPLE 6

Figure 14:
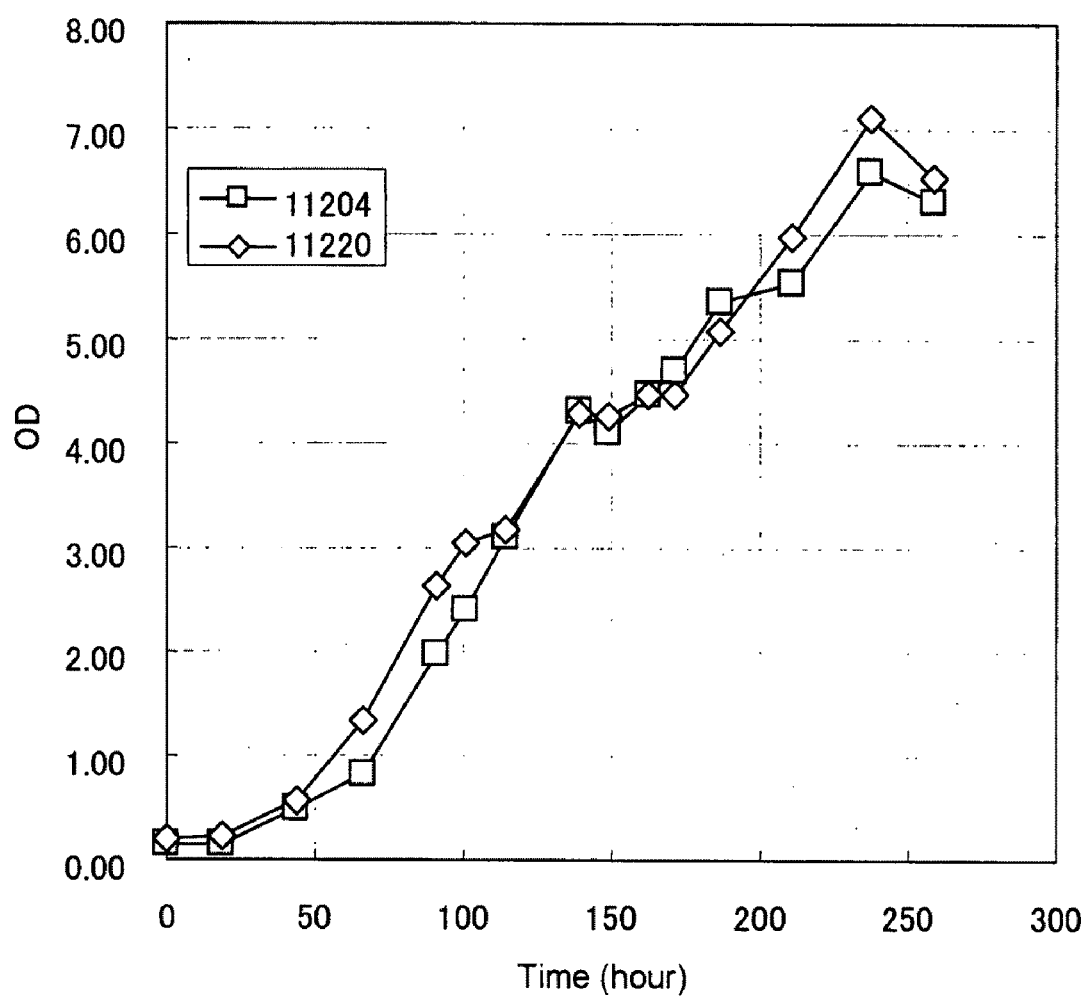
FIG. 14 shows growth curves of an MBIC11220 strain and the MBIC11204 strain, with absorbance at 720 nm as an index (rhombus: MBIC11220 strain, square: MBIC11204 strain).

An MBIC11220 strain was cultured in an A5 medium having the composition shown in the Table 2 above under the same culture conditions as in Example 1. The result is shown in FIG. 14. Absorbance at 720 nm was measured over time as an index of a cell concentration, and a growth curve was drawn. FIG. 14 also shows the growth of the MBIC11204 strain cultured under the same conditions. Both of the strains exhibited very similar growth under these experimental conditions.

Hydrocarbons were extracted from the cells of the MBIC11220 strain obtained in this culture and analyzed in the same way as in Example 2. As a result, the hydrocarbons were presumed to be 4 kinds of hydrocarbons, n-heptadecene ($C_{17}H_{34}$), n-heptadecane ($C_{17}H_{36}$), n-nonadecene ($C_{19}H_{38}$), and n-nonadecane ($C_{19}H_{40}$)

The hydrocarbons confirmed in these Examples to be produced by the culture of the strains MBIC11204, MBIC11220, SAG251-1, and SAG17.98 are summarized in Table 6 below.

TABLE 6

| | 17:1 | 17:0 | 18:1 | 18:0 | 19:1 | 19:0 | 20:2 | 21:1 | 23:1 |
|---|---|---|---|---|---|---|---|---|---|
| | | | *P. ellipsoidea* | | | | | | |
| MBIC11204 | + | + | + | + | + | + | + | | |
| MBIC11220 | + | + | | | + | + | | | |
| | | | *C. minor* | | | | | | |
| SAG251-1 | | + | | | + | | | + | |
| | | | *C. minor* | | | | | | |
| SAG17.98 | | + | | | + | | | + | + |

All publications, patents, and patent applications cited herein are incorporated herein by reference in their entirety.

INDUSTRIAL APPLICABILITY

The present invention provides a novel microalga having the ability to produce hydrocarbons. The hydrocarbon produced by the microalga is available as an alternative fuel to a diesel fuel (light oil). Thus, the present invention is quite useful as a system for producing hydrocarbons without carbon dioxide emissions and environmental loads.

---

The invention claimed is:

1. An isolated and purified novel microalga *Pseudochoricystis ellipsoidea* Sekiguchi et Kurano gen. et sp. nov. MBIC11204 strain deposited at the National Institute of Advanced Industrial Science and Technology under Accession Number FERM BP-10484.

2. An isolated and purified novel microalga *Pseudochoricystis ellipsoidea* Sekiguchi et Kurano gen. et sp. nov. MBIC11220 strain deposited at the National Institute of Advanced Industrial Science and Technology under Accession Number FERM BP-10485.

3. A process for producing hydrocarbons, comprising culturing a *Pseudochoricystis ellipsoidea* Sekiguchi et Kurano gen. et sp. nov. MBIC11204 strain deposited at the National Institute of Advanced Industrial Science and Technology under Accession Number FERM BP-10484, and collecting the hydrocarbon from the resulting cultured product, wherein the hydrocarbons are selected from the group of n-heptadecene, n-heptadecane, n-octadecene, n-octadecane, n-nonadecene, n-nonadecane, and n-eicosadienes.

4. A process for producing hydrocarbons, comprising culturing a *Pseudochoricystis ellipsoidea* Sekiguchi et Kurano .gen. et sp. nov. MBIC11204 strain deposited at the National Institute of Advanced Industrial Science and Technology under Accession Number FERM BP-10485, and collecting the hydrocarbon from the resulting cultured product, wherein the hydrocarbons are selected from the group of n-heptadecene, n-heptadecane, n-nonadecene, and n-nonadecane.

5. The process according to claim 3 or 4, wherein the culture is performed under nitrogen-deficient conditions.

* * * * *

UNITED STATES PATENT AND TRADEMARK OFFICE
CERTIFICATE OF CORRECTION

| | | |
|---|---|---|
| PATENT NO. | : 7,981,648 B2 | Page 1 of 1 |
| APPLICATION NO. | : 11/918374 | |
| DATED | : July 19, 2011 | |
| INVENTOR(S) | : Norihide Kurano et al. | |

It is certified that error appears in the above-identified patent and that said Letters Patent is hereby corrected as shown below:

On the Title Page, Item (54) & Col. 1 line 1, Title: insert --NOVEL-- before "MICROALGA"

Col. 1, line 1, insert --NOVEL-- before "MICROALGA"

Col. 18, line 28, claim 4, "MBIC11204" should be --MBIC 11220--

Signed and Sealed this
Thirteenth Day of December, 2011

David J. Kappos
*Director of the United States Patent and Trademark Office*

UNITED STATES PATENT AND TRADEMARK OFFICE
CERTIFICATE OF CORRECTION

PATENT NO. : 7,981,648 B2  Page 1 of 1
APPLICATION NO. : 11/918374
DATED : July 19, 2011
INVENTOR(S) : Norihide Kurano et al.

It is certified that error appears in the above-identified patent and that said Letters Patent is hereby corrected as shown below:

Title Page, Item (54) and at Column 1, line 1, Title, the word "NOVEL" (as inserted by the Certificate of Correction issued December 13, 2011) should be deleted and title is reinstated to read -- MICROALGA AND PROCESS FOR PRODUCING HYDROCARBON --.

Signed and Sealed this
Tenth Day of January, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 1243
<212> TYPE: DNA
<213> ORGANISM: Unknown
<220> FEATURE:
<223> OTHER INFORMATION: Description of Unknown Organism: novel
      microalgae (Pseudochoricystis ellipsoidea)

<400> SEQUENCE: 1

```
gttgggggct cgaagacgat tagataccgt cctagtctca accataaacg atgccgacta    60
gggattggcg ggcgttcttt tgatgacccc gccagcacct tatgagaaat caaagttttt   120
gggttccggg gggagtatgg tcgcaaggct gaaacttaaa ggaattgacg gaagggcacc   180
accaggcgtg gagcctgcgg cttaatttga ctcaacacgg gaaaacttac caggtccaga   240
catagtgagg attgacagat tgagagctct ttcttgattc tatgggtggt ggtgcatggc   300
cgttcttagt tggtgggttg ccttgtcagg ttgattccgg taacgaacga gacctcagcc   360
tgctaactag tcacgattgg ttcttccagt cggccgactt cttagaggga ctattggcga   420
ctagccaatg gaagtgtgag gcaataacag gtctgtgatg cccttagatg ttctgggccg   480
cacgcgcgct acactgatgc aatcaacgag cctagccttg gccgacaggt ccgggtaatc   540
tttgaaactg catcgtgatg gggatagatg attgcaatta ttcatcttca acgaggaatg   600
cctagtaagc gcgagtcatc agctcgcgtt gattacgtcc ctgcccttg  tacacaccgc   660 ccgtcgctcc taccgattgg gtgtgctggt gaagcgttcg gattggcggc agtgcgcggt   720
tcgccgctcg ctgcagccga gaagttcgtt aaaccctccc acctagagga aggagaagtc   780
gtaacaaggt ttccgtagaa tcaatgcatc accatgcgga agagagcgtg aaagctagtg   840
gggctctctt tgagccctgc gacactgtca aattgcctgg aactcccgct aagtcggcgc   900
caccgctgtg atcgggaaac ctttcgcagc accgcgggta acgcccgcgg gtatggtaac   960
agggcgccga atagggacga tgggcagcca agtcctaagg gcgatttctc gtctacggat  1020
```

```
gcagttcaca gactaaacgg cagtgggttc cagacgtccc gtatgttcac atcgccagga      1080
ctccttggtg ctgatgagct cagaacggtc gggagcttaa gatatagtcg gaccgccccg      1140 gaagggagc caacgggagg atctgtgaag acagagagag cccattggga gcggcctagt       1200
agttgtcggg gcgacccggt caacggcagt cactgctgac ggc                        1243
```

<210> SEQ ID NO 2
<211> LENGTH: 1092
<212> TYPE: DNA
<213> ORGANISM: Unknown
<220> FEATURE:
<223> OTHER INFORMATION: Description of Unknown Organism: novel
      microalgae (Pseudochoricystis ellipsoidea)
<220> FEATURE:
<221> NAME/KEY: misc_feature
<222> LOCATION: (619)..(619)
<223> OTHER INFORMATION: n is a or g or c or t/u or is missing or
      absent

<400> SEQUENCE: 2

```
ttcaagcggt gttaaagatt accgattaac ctactacact ccagattacc aagtaaagga       60
aacagacatc ttggctgctt tccgtatgac acctcaacca ggtgttccgc cagaagagtg      120
cggtgcagcg gttgcagcag aatcgtcaac tggtacttgg actacagttt ggactgatgg      180
tttgactagt cttgacagat acaaaggtcg ttgctatgac atcgagccgg ttcctggtga      240
agacaaccaa tacatcgcat atgttgcgta cccgctagat cttttttgaag agggatcagt     300 tacaaacttg tttacatcta ttgtagggaa cgttttcggt ttcaaagcac ttcgtgcatt     360
gcgtcttgaa gaccttcgca tcccacctgc ttacgtaaaa accttccaag gaccgcctca     420
cggtatccag gttgagcgtg acaaactaaa caagtacggc cgttctttgt tgggttgtac     480
catcaagcca aaactaggtc tttctgctaa gaactacggg cgtgcagtgt acgaatgttt     540
gcgcggtggc ttggatttta cgaaagatga cgaaaacgta aactcacaac catttatgcg     600
ttggagagac cgtttcctnt tttgtttcag aagctattta taaagctcaa gctgagacag     660
gtgaggttaa gggtcactac ctaaacgcga ctgctggtac ttgtgaagag atgctaaaac     720
gtgctgagtc tgcgaaagac tttggtgttc aatcattat gcatgactac ctaactggtg      780
gtttcactgc aaacacttca ttggcacact actgccgtga caacagcctt ttgcttcaca     840
ttcaccgtgc gatgcacgct gttattgacc gtcaacgtaa ccacggtatg cacttccgtg     900
ttcttgcaaa agctcttcgt ttgtctggtg gtgaccacct tcactcaggt accgttgtag     960
gtaaacttga gggagaacgt gaggtaaccc taggtttcgt tgacctaatg cgtgacgact     1020
acattgagaa agacagaagc cgaggcatct acttcactca agactgggta tctcttcctg     1080
gtgttatgcc ag                                                         1092
```

<210> SEQ ID NO 3
<211> LENGTH: 1754
<212> TYPE: DNA
<213> ORGANISM: Unknown
<220> FEATURE:
<223> OTHER INFORMATION: Description of Unknown Organism: novel
      microalgae (Pseudochoricystis ellipsoidea)

<400> SEQUENCE: 3

```
tagtcatatg cttgtctcaa agattaagcc atgcatgtct aagtataaac tgctttatac       60
tgtgaaactg cgaatggctc attaaatcag ttatagttta tttgatggta ccttactact      120
cggataaccg tagtaattct agagctaata cgtgcggaaa tcccgacttc tggaagggac      180
gtatttatta gataaaaggc cgaccgggct tgcccgaaac gcggtgaatc atgataactc      240
```

```
cacgaatcgc atggcctcag cgccggcgat gtttcattca aatttctgcc ctatcaactt    300
tcgacggtaa ggtattggct taccgtggtg gtaacgggtg acggaggatt agggttcgat    360
tccggagagg gagcctgaga aacggctacc acatccaagg aaggcagcag gcgcgcaaat    420
tacccaatct tgacacaagg aggtagtgac aataaataac aataccgggg ttttcaact     480 ctggtaattg gaatgagtac aatctaaacc ccttaacgag gatcaattgg agggcaagtc    540
tggtgccagc agccgcggta attccagctc caatagcgta tatttaagtt gttgcagtta    600
aaaagctcgt agttggattt cgggcgggcc cggccggtcc gcctttgggt gtgcactgac    660
cgggcccgtc ttgttgccgg ggacgggctc ctgggcttaa ctgtccggga ctcggagtcg    720
gcgaggttac tttgagtaaa ttagagtgtt caaagcaggc ctacgctctg aatacattag    780
catggaataa cacgatagga ctctggccta tcttgttggt ctgtgggacc ggagtaatga    840
ttaagaggga cagtcggggg cattcgtatt tcattgtcag aggtgaaatt cttggattta    900
tgaaagacga actactgcga aagcatttgc caaggatgtt ttcattaatc aagaacgaaa    960
gttgggggct cgaagacgat tagataccgt cctagtctca accataaacg atgccgacta   1020
gggattggcg gcgttctttt tgatgacccc gccagcacct tatgagaaat caaagttttt   1080
gggttccggg gggagtatgg tcgcaaggct gaaacttaaa ggaattgacg gaagggcacc   1140
accaggcgtg gagcctgcgg cttaatttga ctcaacacgg gaaaacttac caggtccaga   1200
catagtgagg attgacagat tgagagctct ttcttgattc tatgggtggt ggtgcatggc   1260
cgttcttagt tggtgggttg ccttgtcagg ttgattccgg taacgaacga gacctcagcc   1320
tgctaactag tcacgattgg ttcttccagt cggccgactt cttagaggga ctattggcga   1380
ctagccaatg gaagtgtgag gcaataacag gtctgtgatg cccttagatg ttctgggccg   1440
cacgcgcgct acactgatgc aatcaacgag cctagccttg gccgacaggt ccgggtaatc   1500
tttgaaactg catcgtgatg gggatagatg attgcaatta ttcatcttca acgaggaatg   1560
cctagtaagc gcgagtcatc agctcgcgtt gattacgtcc ctgccctttg tacacaccgc   1620
ccgtcgctcc taccgattgg gtgtgctggt gaagcgttcg gattggcggc agtgcgcggt   1680
tcgccgctcg ctgcagccga gaagttcgtt aaaccctccc acctagagga aggagaagtc   1740
gtaacaaggt ttcc                                                    1754
```

<210> SEQ ID NO 4
<211> LENGTH: 1087
<212> TYPE: DNA
<213> ORGANISM: Unknown
<220> FEATURE:
<223> OTHER INFORMATION: Description of Unknown Organism: novel
     microalgae (Pseudochoricystis ellipsoidea)

<400> SEQUENCE: 4

```
caagcaggtg ttaagattac cgattaacct actacactcc agattaccaa gtaaaggaaa     60
cagacatctt ggctgctttc cgtatgacac ctcaaccagg tgttccgcca gaagagtgcg    120
gtgcagcggt tgcagcagaa tcgtcaactg gtacttggac tacagtttgg actgatggtt    180
tgactagtct tgacagatac aaaggtcgtt gctatgacat cgagccggtt cctggtgaag    240
acaaccaata tcgcatat gttgcatacc cgctagatc ttttgaagag ggatcagtta     300
caaacttgtt tacatctatt gtagggaacg ttttcggttt caaagcactt cgtgcattgc    360
gtcttgaaga ccttcgcatc ccacctgctt acgtcaaaac cttccaagga ccgcctcacg    420
gtatccaggt tgagcgtgac aaactaaaca agtacggccg ttctttgtta ggttgcacca    480
```

```
tcaagccaaa actaggtctt tctgctaaga actacgggcg tgcagtgtac gaatgtttac    540
gtggtggctt agattttacg aaagacgacg agaacgtaaa ctcacaacca tttatgcgtt    600
ggagagaccg tttccttttc gtttcagaag ctatctacaa agctcaagct gagacaggtg    660
aggttaaagg tcactaccta aacgcgactg ctggtacttg tgaagagatg ctaaaacgtg    720
ctgagtctgc gaaagacttt ggtgttccaa tcattatgca tgactaccta actggtggtt    780
tcactgctaa cacttcattg gcacactact gccgtgacaa cagccttttg cttcacattc    840
accgtgcgat gcacgctgtt attgaccgtc aacgtaacca cggtatgcac ttccgtgttc    900
ttgcgaaagc tcttcgtttg tctggtggtg accaccttca ctcaggtacc gttgtaggta    960
aacttgaggg agaacgtgaa gtaaccctag gtttcgttga cctaatgcgt gacgactaca   1020
ttgagaaaga cagaagccga ggcatctact tcactcaaga ctgggtatct cttcctggtg   1080
tatgcca                                                             1087
```